United States Patent
Shim

(10) Patent No.: US 6,254,858 B1
(45) Date of Patent: Jul. 3, 2001

(54) HAIR TREATMENT COMPOSITION CONTAINING LOESS, ARTEMESIA, BROWN ALGAE AND PINE JUICES

(75) Inventor: Ho Chin Shim, Kyounggi-Do (KR)

(73) Assignee: Da Min Enterprise, Ltd. (KR)

( * ) Notice: Subject to any disclaimer, the term of this patent is extended or adjusted under 35 U.S.C. 154(b) by 0 days.

(21) Appl. No.: 09/184,599

(22) Filed: Nov. 2, 1998

(30) Foreign Application Priority Data

Nov. 3, 1997 (KR) .................................................. 97-57760

(51) Int. Cl.$^7$ ...................................................... A61K 7/06
(52) U.S. Cl. .................. 424/70.1; 424/74; 424/195.1; 424/196; 424/70.14; 514/880
(58) Field of Search ............... 424/195.1, 196.1, 424/70.1, 74, 70.14; 514/880

(56) References Cited

U.S. PATENT DOCUMENTS 5,108,749 * 4/1992 Hua .................................... 424/196.1
5,674,510   10/1997 DiTucci ................................ 424/401

FOREIGN PATENT DOCUMENTS

| 1089133 | * | 3/1996 | (CN) . |
| 2310770 | * | 12/1976 | (FR) . |
| 2318620 | * | 2/1990 | (FR) . |
| 6183932 | * | 7/1994 | (JP) . |
| 8073324 | * | 3/1996 | (JP) . |

* cited by examiner

Primary Examiner—Thurman K. Page
Assistant Examiner—Lakshmi Channavajjala
(74) Attorney, Agent, or Firm—Cook, Alex, McFarron, Manzo, Cummings & Mehler Ltd.

(57) ABSTRACT

The present invention relates to hair treatment compositions and methods of manufacturing the compositions, which are capable of acting as a cosmetic, reducing alopecia, preventing alopecia, stimulating hair growth or any combination thereof. The hair treatment composition comprises loess juice, brown algae juice, artemisia juice, pine leaves juice, and additives.

12 Claims, 2 Drawing Sheets

HAIR TREATMENT COMPOSITION CONTAINING LOESS, ARTEMESIA, BROWN ALGAE AND PINE JUICES

DESCRIPTION

BACKGROUND OF THE INVENTION

1. Field of the Invention

The present invention relates to hair treatment compositions and methods of manufacturing the compositions, and more specifically to such compositions which are capable of acting as a cosmetic, reducing alopecia, preventing alopecia, stimulating hair growth or any combination thereof, as well as methods of manufacturing the compositions.

2. Description of the Prior Art

Alopecia can be caused by various factors including, but not limited to, mental stress, hormonal imbalances, chemotherapy and febrile conditions. Alopecia is also attributed to advancing age and a decrease in the mitotic activity of the hair follicle.

Due to society's tendency to attach a stigma to hair loss, there exists a substantial demand for a "cure" to baldness. In particular, the desire to maintain a full head hair has resulted in numerous hair growth studies. These studies have led to several causes with respect to the acquired loss of hair.

Particularly, among the several causes, a hypothesis that seborrhea leads to alopecia is generally accepted now. As illustrated in FIG. 1, a hair 1 is composed of a hair bulb 4 which includes stem cells 3 having hair papillas 2 provided to nutrients through a blood vessel, a hair root 6 which has sebaceous glands 5 located in a part connected to the stem cells, and a hair shaft 8 which is one part of scalp 7.

Though sebum makes hair glaze by nature, if excessive secreting sebum oxygenates to peroxide of lipid, sebum changes to seborrhea which hardened like a wax. The seborrhea mostly stops up hair bulbs, resulting in reduction of the metabolism of the stem cell and stoppage of hair generation. If these phenomena continue in the scalp, seborrhea becomes scurfy and hair removal from the scalp is increased; that is, alopecia occurs.

On the other hand, it was known that there are many compositions and treatments for curing alopecia in the prior art. For example, these include a composition mixed with various herbs, a composition made from a polysaccharide which is extracted from the skin of animals, and a composition made from a minoxydyl used as hyperpiesia remedy, etc. Also, there are treatments such as stimulating a blood vessel by using the art of acupuncture and planting follicles in the scalp directly.

But it remains a challenge in the art to provide a composition that is capable of reducing and/or preventing alopecia without any detrimental side effects. It is a further challenge in the art to provide a composition that is capable of increasing hair growth or acting as a cosmetic without inducing negative side effects.

SUMMARY OF THE INVENTION

Accordingly, it is an object of the present invention to provide a hair treatment composition and method of manufacturing the composition that is capable of acting as a cosmetic, reducing and preventing alopecia by melting seborrhea and keeping hair bulbs open.

It is another object of the present invention to provide a hair treatment composition, and method of manufacturing the composition, that is capable of acting as a cosmetic and increasing hair growth to epithelia of follicles directly and by stimulating a peripheral blood vessel system.

A hair treatment composition and method of manufacturing the composition according to the present invention is made by and includes the steps of extracting juice contained various components from loess, brown algae, artemisia, and leaves of pine tree.

In a preferred embodiment, the step of extracting loess juice from the loess includes a step of separating minute loess by means of pulverizing the loess and screening the pulverized loess, and a step of separating only loess solution including $SiO_2$, Al, Mg, and various minerals, after dissolving the minute loess in purified water.

In a preferred embodiment, the step of extracting brown algae juice from the brown algae includes a step of extracting brown algae juice from the brown algae by means of heating, a step of extracting brown algae juice from the brown algae by means of not heating but breaking tissues of the brown algae, pulverizing the broken tissues, and filtering the pulverized tissues, and a mixing step of mixing the brown algae juice extracted by the heating step with the brown algae juice extracted by the non-heating step.

In a preferred embodiment, the brown algae includes brown seaweeds and kelps. In a preferred embodiment, the non-heating step of extracting a brown algae juice includes a deodorizing step of removing odor from brown algae, a breaking step of breaking tissues of the brown algae so as to be easy to extract juice, a pulverizing step of pulverizing the broken tissues using a pulverizer, and a filtering step of filtering the pulverized tissues.

In a preferred embodiment, the breaking step includes a few repeated operations of thawing after freezing.

In a preferred embodiment, the step of extracting artemisia juice from artemisia sources includes a pulverizing step of pulverizing the artemisia, a cooling step of cooling the brown algae juice gained in the heating step until its temperature is about 60° C., and an extracting step of extracting the artemisia juice by means of putting the pulverized artemisia in the cooled brown algae juice and leaving it until a component including cineole and sesquiterpene, etc. are evident.

In a preferred embodiment, the step of extracting pine leaf juice from the needles of pine trees includes a heating step of heating a mixture which is mixed with the pine needles in water and a step of extracting pine leaf juice from the heated mixture.

DESCRIPTION OF THE PREFERRED EMBODIMENTS

Figure 1:
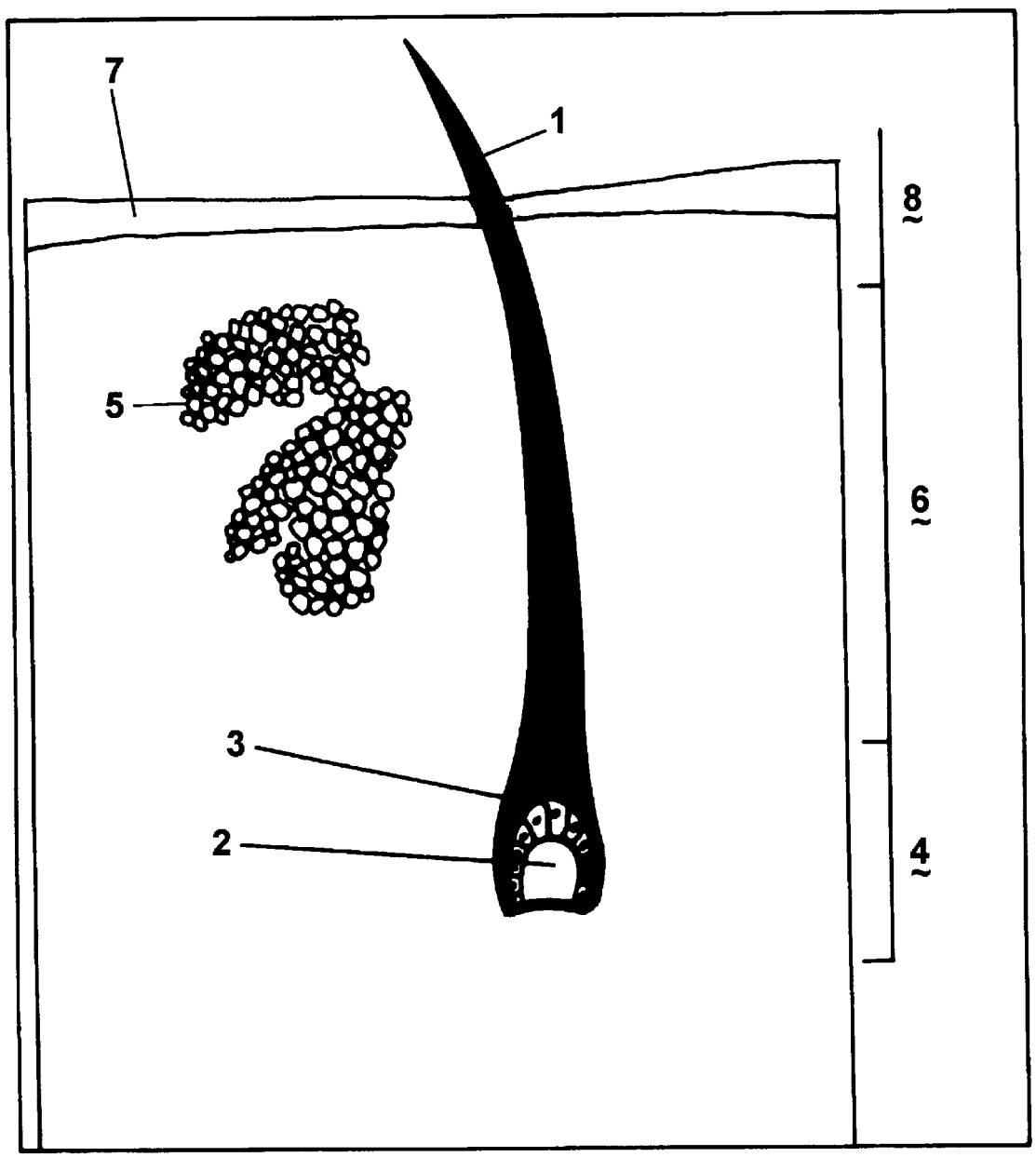
FIG. 1 is a structural view of hair which is provided to describe a theoretical base of a hair treatment composition according to the present invention.

Hereinafter, hair treatment compositions and methods of manufacturing the compositions according to the present invention will be described in detail.

The hair treatment composition according to the present invention is capable of acting as a cosmetic, reducing alopecia, preventing alopecia, increasing hair growth or any combination thereof. The hair treatment composition comprises a combination of extracts including a plurality of loess juice, brown algae juice, artemisia juice, pine leaf juice, and additives.

Any amount of the loess extract may be included within the hair treatment composition according to the present invention. A typical range is between about 30 to about 60 weight percent, based on the total weight of the composition. The loess juice includes $SiO_2$, Al, Mg, and various minerals. "Loess" as used herein refers to loamy type soils that include easily crumbed mixtures of varying proportions of sands, silt, clay and yellow earth whose particle size is from about 0.02 mm to about 0.05 mm, water content is about 10% to about 15% by weight, and its empty space porosity is about 50% to about 55%. The chemical composition of the loess follows: $SiO_2$ about 50% to about 60%, $Al_2O_3$ about 8% to about 12%, $Fe_2 O_3$ (III) about 2% to about 4%, FeO (II) about 0.8% to about 1.1%, $TiO_2$ about 0.5%, MnO about 0.5%, CaO about 4% to about 16%, and MgO about 2% to about 6%, all being percents by weight.

The step of extracting the loess juice including $SiO_2$, Al, Mg, and various minerals from the loess includes a step of separating the minute loess by means of pulverizing the loess and screening the pulverized loess, a step of separating only loess solution including $SiO_2$, Al, Mg, and various minerals, after dissolving the minute loess in purified water and a step of extracting the loess juice by means of taking the upper portion of the stirred loess solution which is kept in a dark place after stirring the loess solution with a wooden stick.

Also, any amount of the brown algae extract may be included within the hair treatment composition according to the present invention. A typical range is between about 30 and about 60 weight percent, based on the total weight of the composition. The brown algae juice or extract includes various minerals, especially, a plurality of Ca and I. In particular Ca and I act to control hormone secretion, particularly secretion of the thyroid gland related to hair growth. Examples of genus or species designations of brown algae include *Andarea pinnatifida, Laminaria japonica* and *Fucus vesiculosus*.

The method of extracting the brown algae juice from the brown algae uses a heating method which is capable of extracting iodine smoothly together with a non-heating method which is capable of extracting other components smoothly by means of breaking tissues of the brown algae with repeatedly thawing the frozen tissues after freezing and refreezing the tissues.

The heating method includes a step of mixing the brown algae in water, a step of heating the mixture during about 2 to about 3 hours, and a step of extracting the brown algae juice from the heated mixture. And the non-heating method includes a deodorizing step of removing a brown algae odor, a step of breaking the tissues of the brown algae by means of repeatedly thawing the frozen tissues after freezing the tissues, a step of pulverizing the broken tissues using a pulverizer so as to break more than 90% of the tissue, and a step of extracting the brown algae juice by means of filtering the pulverized tissues.

In the step of breaking the tissues, a temperature of freezing ranges from about −7 to about −3° C., and a temperature of thawing ranges from about +1 to about +5° C. In particular, when the temperature of freezing is about −7° C. and the temperature of thawing is about +5° C., the tissue is broken most effectively. Additionally, the brown algae condition is not limited as long as the particles remain as brown algae.

Also, any amount of the artemisia extract may be included within the hair treatment composition according to the present invention. A typical range is between about 5 and about 20 weight percent, based on the total weight of the composition. The artemisia includes various components including cineole and sesquiterpene, etc. The cineole and sesquiterpene act to enhance a cell repairing system, increase red blood cells and antibodies, and prevent or reduce skin from aging. Artemisia are herbs and shrubs of the genus Artemisia, typically having strong-smelling foliage. Common names for members of this genus include wormwood, wormseed, southern wood, and Artemisia Cina Berg.

The step of extracting the artemisia juice from the artemisia includes a drying step of drying the artemisia in a dark place, a pulverizing step of pulverizing the dried artemisia, a cooling step of cooling the brown algae juice gained in the heating method until its temperature is about 60° C., and an extracting step of extracting the artemisia juice by means of putting the pulverized artemisia in the cooled brown algae juice and leaving it until its various components, including cineole, sesquiterpene, and various medicinal components, are evident.

Also, any amount of the pine leaf extract may be included within the hair treatment composition according to the present invention. Suitable sources are pine leaves or needles of coniferous evergreen trees. The chemical composition of pine leaves per 100 g includes water 58.1 g, protein 4.5 g, fat 3.9 g, saccharide 19.6 g, fibroid material 13.3 g, lime 0.6 g, Ca 61 mg, P 51 mg, Fe 3.1 mg, vitamin A 5.165 I.U., niacin 0.2 mg, vitamin B1 0.70 mg, vitamin B2 0.16 mg, vitamin C 29 mg, etc). Typical amounts of the pine needle extract or juice is between about 5 to about 20 weight percent, based on the total weight of the composition.

It is known that components of pine leaves, onion, red pepper, ginger, ginkgo leaves, garlic, and leaves of spindle tree stimulate hair growth. So as to know what is effective to grow hairs, after extracting juices respectively, samples of a hair treatment compositions were made by means of mixing the loess juice, the brown algae juice, the artemisia juice and the pine leaves juice with the above extracted juices of them respectively. The samples were given to 10 persons for trials each having a duration of 3 months. The results indicated that both of the sample pine leaf juice mixtures and the sample ginger juice mixtures clearly stimulated hair growth. But ginger is more expensive than pine leaves. Therefore, the hair treatment composition according to the present invention uses the pine leaf juice.

Figure 2:
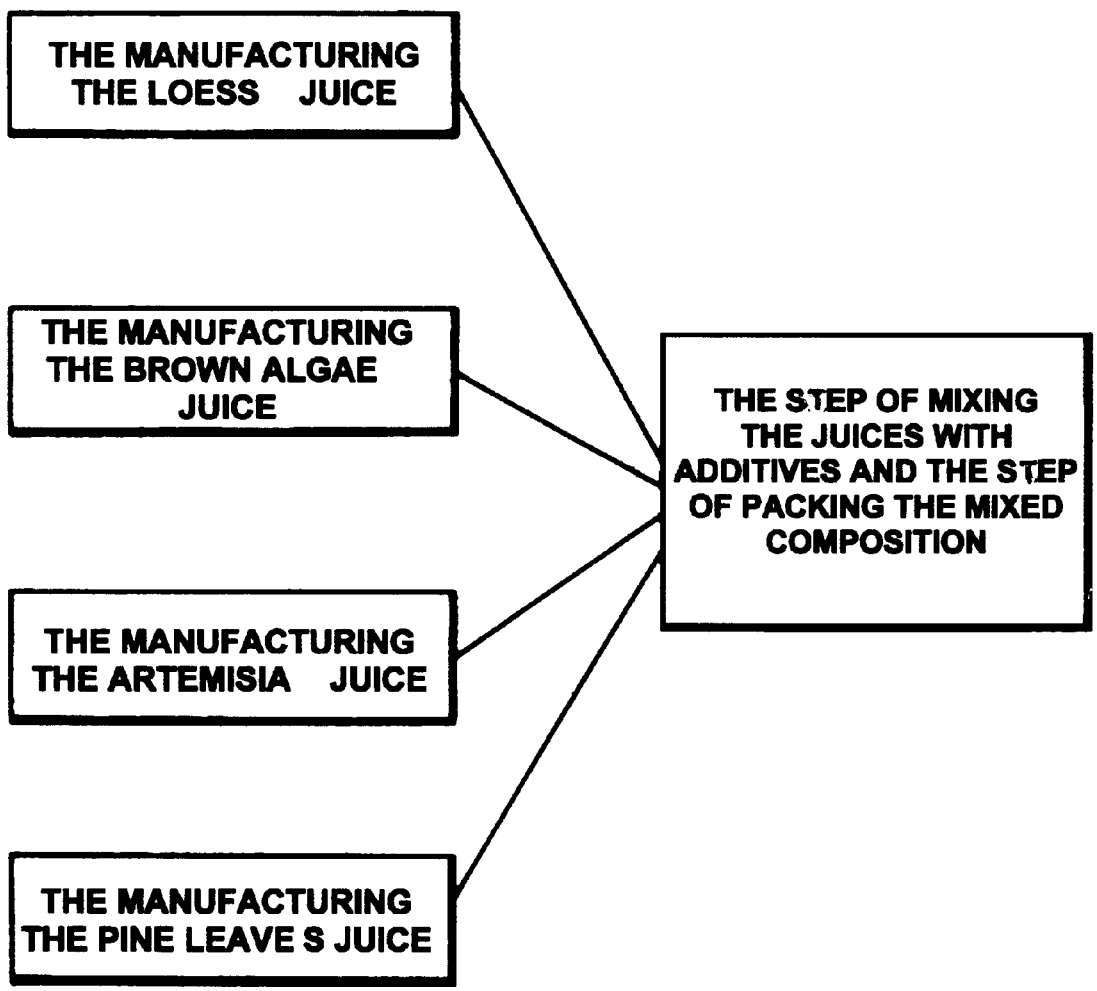
FIG. 2 is a schematic view of a method of manufacturing the hair treatment compositions according to the present invention.

As illustrated schematically in FIG. 2, the preferred method of manufacturing the hair treatment composition according to the present invention includes the step of manufacturing the loess juice by means of extracting the loess juice from the loess, the step of manufacturing the brown algae juice by means of extracting the brown algae juice from the brown algae, the step of manufacturing the artemisia juice by means of extracting the artemisia juice from the artemisia, and the step of manufacturing the pine leaves juice by means of extracting the pine leaf juice from the pine leaves. Also, the method of manufacturing the hair treatment composition includes a step of mixing the loess juice, the brown algae juice, the artemisia juice, the pine leaves juice and additives so as to make the hair treatment composition according to the present invention, followed by a step of packaging the hair treatment composition thus formed.

EXAMPLES

Hereinafter, examples of the present invention will be described. However, the present invention is not limited by the examples.

1. Extraction of loess juice including $SiO_2$, Al, Mg, and various minerals:

A minute loess in the amount of 100 g was prepared by means of pulverizing loess and screening the pulverized loess. After the 100 g minute loess was dissolved in 500 mg of purified water, a loess solution primarily only $SiO_2$, Al, and Mg, etc. was separated. The loess solution was kept for about 1 hour in a dark place after stirring the loess solution with a wooden stick. Finally, the loess juice was extracted by means of taking the upper portion of the loess solution.

2. Extraction of brown algae juice including various minerals:

2.1 As raw material, brown seaweeds and kelps were selected as the brown algae, and their amount was about 2 kg in raw form.

2.2 Extraction of the brown algae juice can include heating. The brown algae juice was extracted by means of heating during about 3 hours to about 4 hours after adding 1 kg of the brown seaweeds and kelps in 4 liters of water.

2.3 Extraction of the brown algae juice by means of non-heating is as follows. To remove odors attendant to brown algae, the rest of the brown seaweeds and kelps (about 1 kg) were washed for about 1 hour.

The deodorized brown seaweeds and kelps were frozen at −5° C. for 3 hours, and then the frozen brown seaweeds and kelps were thawed at +3° C. for about 3 hours. When the above mentioned handling was repeated about three times, tissues of the brown seaweeds and kelps were broken to about 50%. The broken tissues were pulverized by using a pulverizer so as to break the tissues to more than 90%. The brown algae juice was extracted by means of filtering the pulverized tissues. Lastly, the brown algae juice was extracted by non-heating at a weight ratio of 1:1.

3. Extraction of artemisia juice:

Artemisia was dried in darkness. About 1 kg of the dried artemesia was pulverized with a pulverizer. The artemisia juice was extracted by means of putting the pulverized artemisia in the cooled brown algae juice whose temperature was about 60° C. and leaving it until a various components including cineole and sesquiterpene, etc. were dissolved. Herein, the weight ratio of the pulverized artemisia and the cooled brown algae juice was 1 to 100.

4. Extraction of pine needle juice:

Leaves or needles of pine trees (about 500 g) were mixed with about 4 liters of water. The mixture was heated until the amount of the mixture was about 1 liter. Then the pine needle juice was extracted from the heated mixture.

5. A hair treatment composition including the loess juice, the brown algae juice, the artemisia juice, the pine needle juice and additives:

The hair treatment composition was manufactured by mixing the loess juice, the brown algae juice, the artemisia juice, the pine needle juice and additives uniformly in order, according to the following Table 1. This lists raw material amounts as respective weight parts with respect to about 10 weight parts of the artemisia juice (when present).

TABLE 1

| Raw material | hair treatment composition A | comparative Example 1 | comparative Example 2 | comparative Example 3 | comparative Example 4 |
|---|---|---|---|---|---|
| loess juice | 50 | — | 50 | 50 | 50 |
| brown algae juice | 50 | 50 | 50 | 50 | — |
| artemisia juice | 10 | 10 | 10 | — | 10 |
| pine needle juice | 20 | 20 | — | 20 | 20 |
| propyl paraoxybenzoic acid | 0.01 | 0.01 | 0.01 | 0.01 | 0.01 |
| colorant | a proper quantity | a proper quantity | a proper quantity | a proper quantity | a proper quantity |
| aromatic oils | 0.01 | 0.01 | 0.01 | 0.01 | 0.01 |

The hair treatment composition "A" according to the invention and the comparative Examples 1, 2, 3, and 4 manufactured according to Table 1 were applied to 30 users. The test results were valued at 1 to 5, and an average value was taken. These values are reported in Table 2. If the average value was 5, this indicated a test result which was very good. If the average value was 4, this indicated a test result which was good. If the average value was 3, this indicated a test result which was ordinary. If the average value was 2, this indicated a test result which was bad. If the average value was 1, this indicated a test result which was worse.

TABLE 2

| Property | the hair treatment composition A | comparative Example 1 | comparative Example 2 | comparative Example 3 | comparative Example 4 |
|---|---|---|---|---|---|
| a regeneration of the portion of alopecia | 3.2 | 2.8 | 2.5 | 3.0 | 2.8 |
| a preventing ratio of alopecia | 4.4 | 4.0 | 4.0 | 2.5 | 3.0 |
| a removing ratio of lipid | 4.5 | 4.0 | 4.0 | 4.0 | 4.0 |
| a removing ratio of dandruff | 4.5 | 4.3 | 4.2 | 4.2 | 3.8 |
| an improving ratio of the texture of hair | 4.8 | 4.8 | 4.8 | 4.8 | 2.0 |

As described results, the loess juice including $SiO_2$, Al, Mg, and various minerals affected the regeneration of hair and the prevention of alopecia. Also, the brown algae juice was effective in smoothing the texture of the hair.

It will be understood that the embodiments of the present invention which have been described are illustrative of some of the applications of the principles of the present invention. Numerous modifications may be made by those skilled in the art without departing from the true spirit and scope of the invention.

What is claimed is:

1. A hair treatment composition comprising:
   between about 30 and about 60 weight percent of loess juice;

between about 30 and about 60 weight percent of brawn algae juice;

between about 5 and about 20 weight percent of artemisia juice;

between about 5 and about 20 weight percent of pine leaves juice;

all based on the total weight of the composition; and cosmetically acceptable additives, wherein the hair treatment composition is formulated to reduce and prevent alopecia and to stimulate hair growth.

2. The hair treatment composition according to claim 1, wherein the loess juice is an extract which principally includes $SiO_2$, $Al_2O_3$, CaO and MgO.

3. The hair treatment composition according to claim 1, wherein the brown algae juice is extracted from brown seaweeds and kelps including calcium and iodine.

4. The hair treatment composition according to claim 1, wherein the artemisia juice is an extract which includes cineole and sesquiterpene as pharmacologically effective components.

5. The hair treatment composition according to claim 1, wherein the pine leaves juice is an extract which includes proteins, lipids, saccharides, celluloses, Ca, P, Fe, and vitamins A, $B_1$, $B_2$, and C.

6. A hair treatment composition prepared by a process comprising the steps of:

extracting loess juice by pulverizing loess, dissolving same in water to provide a solution, and separating from said solution loess juice having $SiO_2$, $Al_2O_3$, CaO and MgO;

extracting brown algae juice by combining water and brown algae and heating same to extract brown algae juice, and also by breaking brown algae tissue without heating and then collecting brown algae juice, and combining said brown algae juices to provide said brown algae juice of this extracting step;

pulverizing artemisia and extracting artemisia juice;

mixing pine leaves and water and extracting pine leaves juice; and uniformly mixing each said juice with cosmetically acceptable additives, wherein said composition includes between about 30 and about 60 weight percent of each of said loess juice and said brown algae juice, and between about 5 and about 20 weight percent of each of said artemisia juice and said pine leaves juice, all based on the total weight of the composition.

7. A hair treatment composition prepared by a process comprising the steps of:

extracting loess juice, which includes a step of separating minute loess by means of pulverizing loess and screening the pulverized loess, a step of separating only loess solution including $SiO_2$, $Al_2O_3$, CaO and Mgo, after dissolving the minute loess in purified water, and a step of extracting the loess juice by means of taking the upper portion of stirred loess solution which is kept in a dark place after stirring the loess solution;

extracting brown algae juice;

extracting artemisia juice;

extracting pine leaves juice; and uniformly mixing each said juice with cosmetically acceptable additives.

8. A hair treatment composition prepared by a process comprising the steps of:

extracting brown algae juice, which includes a non-heating step of extracting brown algae juice by means of not heating but breaking tissues of brown algae, which non-heating step includes deodorizing to remove an odor by washing brown algae with water for about one hour, breaking tissues of the brown algae by freezing the tissues at a temperature of about −7° C. to about −3° C. for about 3 hours and then thawing the frozen tissues at a temperature of about 1° C. to about 5° C. for about 3 hours repeatedly, pulverizing the broken tissues using a pulverizer, and filtering the pulverized tissues;

extracting loess juice by pulverizing and dissolving loess in water to provide a solution and separating loess juice from the solution;

extracting artemisia juice;

extracting pine leaves juice, and uniformly mixing each said juice with cosmetically acceptable additives.

9. The hair treatment composition according to claim 1, wherein the cosmetically acceptable additives comprise propyl paraoxybenzoic acid, colorant and aromatic oils.

10. The hair treatment composition according to claim 6, wherein the cosmetically acceptable additives comprise propyl paraoxybenzoic acid, colorant and aromatic oils.

11. The hair treatment composition according to claim 7, wherein the cosmetically acceptable additives comprise propyl paraoxybenzoic acid, colorant and aromatic oils.

12. The hair treatment composition according to claim 8, wherein the cosmetically acceptable additives comprise propyl paraoxybenzoic acid, colorant and aromatic oils.

* * * * *